Figure 1:
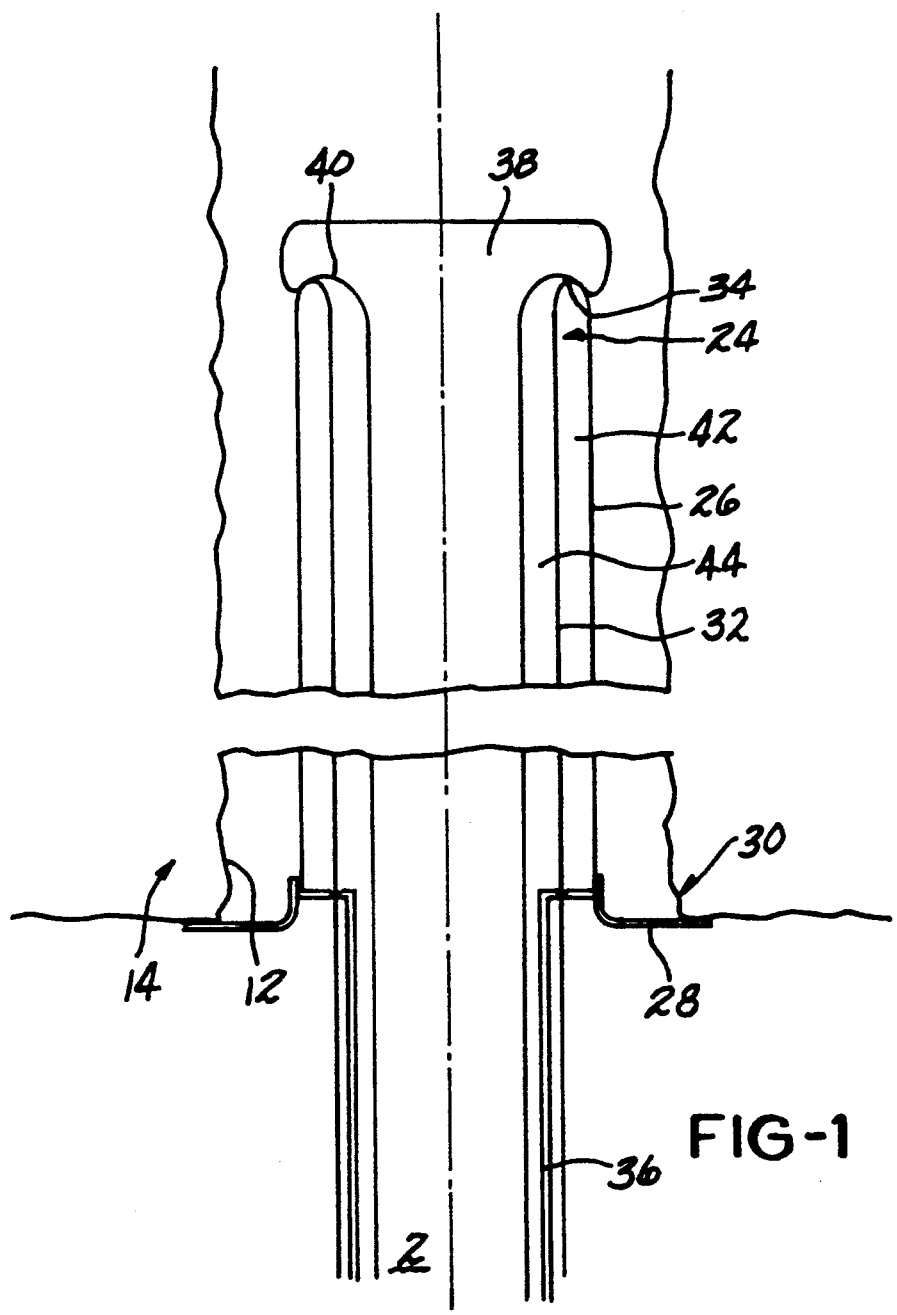

United States Patent [19]

Bob et al.

[11] Patent Number: 5,259,364

[45] Date of Patent: Nov. 9, 1993

[54] ENDOSCOPE DEVICE

[75] Inventors: Alexander Bob; Konstantin Bob, both of Weinheim; Andreas Gründl, München, all of Fed. Rep. of Germany

[73] Assignee: STM Medizintechnik Starnberg GmbH, Starnberg, Fed. Rep. of Germany

[21] Appl. No.: 851,379

[22] Filed: Dec. 24, 1991

[30] Foreign Application Priority Data

Aug. 1, 1989 [DE] Fed. Rep. of Germany ....... 3925484
Aug. 1, 1990 [EP] European Pat. Off. ............ PCT/EP90/01264

[51] Int. Cl.⁵ ............................................. A61B 1/00
[52] U.S. Cl. ...................................... 128/4; 604/271
[58] Field of Search ................ 128/4, 3; 604/271, 96; 606/149

[56] References Cited

U.S. PATENT DOCUMENTS

| 3,982,544 | 9/1976 | Dyck | 604/271 |
| 4,321,915 | 3/1982 | Leighton et al. | 128/4 |
| 4,437,857 | 3/1984 | Goldstein et al. | 604/53 |
| 4,615,331 | 10/1986 | Kramann | 128/4 |
| 5,045,070 | 9/1991 | Grodecki et al. | 604/271 |

FOREIGN PATENT DOCUMENTS

| 2823025 | 12/1979 | Fed. Rep. of Germany | 128/4 |
| 2420351 | 11/1979 | France | 604/271 |

*Primary Examiner*—Richard J. Apley
*Assistant Examiner*—Karen A. Jalbert
*Attorney, Agent, or Firm*—Willam W. Jones

[57] ABSTRACT

An endoscope device includes an endoscope tube having a forward head piece and a flexible eversion tube for moving the head piece into a channel-like body cavity by means of fluid pressure. The eversion tube has an outer portion; a turning portion engaging the head piece; and a rearwardly extending inner portion. A first fluid pressure is exerted in a space between the outer portion and the inner portion of the eversion tube, which space is sealed from ambient surroundings. A second fluid pressure is exerted in a space between the endoscope tube and a rearwardly extending inner portion of the eversion tube.

9 Claims, 2 Drawing Sheets

ENDOSCOPE DEVICE

The invention relates to an endoscope device comprising an endoscope and means for moving the endoscope into a channel-like cavity by means of fluid pressure. The invention relates furthermore to a device for introducing an endoscope into a channel-like cavity by means of fluid pressure, i.e. to the means for moving the endoscope into the channel-like cavity without the endoscope proper being a constituent part of the device as a whole.

The invention is intended for being used in the medical field, in particular for the exploration of cavities or tubular channels of the human body, and in other fields, in particular for the exploration of cavities or tubular channels of technical means. The following description will deal primarily with the medical field.

In the medical field, endoscopes have become particularly established for the exploration of esophagus, stomach, duodenum from the stomach, intestine from the anus, urethra, bladder and ureters. Endoscopes are equipped at their front end with an illumination means and an optical system for visually inspecting the portion of the body cavity or body duct located ahead thereof. While the optical information sensed before the front end of the endoscope until recently was usually transmitted through the endoscope to the rearward operating end by means of a fiber optical system, the latest prior art is constituted by the installation of a camera chip at the forward endoscope end as well as by the electrical image transmission and the presentation of the optical information gained on a screen monitor. Furthermore, endoscopes have as a rule a so-called working passage through which several working utensils can be introduced and operated, such as e.g. small pliers for taking tissue samples, biopsy needles, heatable cutting wires, small scissors, coagulation electrodes or the like.

Finally, there are provided as a rule a fluid channel for rinsing liquid and operating wires for bending the endoscope front end in several directions. Apart from its rear operating end and a connecting cord, the endoscope as a whole has an elongated flexible rod-shaped configuration. Usual outer diameter are approximately in the range from 9 to 15 mm, with somewhat larger dimensions at the front head.

Endoscopes so far are being introduced into the body in that the doctor slidingly introduces the flexurally stiff endoscope into the body from the part of the endoscope extending out of the body. This type of introducing the endoscope is particulary strenuous, difficult and time-consuming in case of a coloscope, especially because the colon has bends and frequently constrictions. Accordingly, coloscopic examinations so far belong to the complex examinations that are unpleasant for the patient, and thus they can hardly be considered for broad application. Handling of a coloscope requires a doctor having experience in this respect.

This situation is particularly disadvantageous since anomalies of the intestinal wall, for instance polyps, adenomas and carcinomas, become increasingly numerous in many parts of the world and since recognition thereof as early as possible enhances the healing chances of the patient concerned quite considerably or results in a considerable prolongation of lifetime, respectively. In so far it is extremely desirable to have available an endoscope which can be introduced in less complicated and faster manner, also by less experienced doctors in the field concerned or by assistant personnel, and the introduction of which is less strenuous for the patient. For the reasons mentioned, this applies in particular for coloscopes.

Subject matter of the invention is on the one hand an endoscope device comprising the following features:
a) an endoscope tube having a forward head piece,
b) a flexible eversion tube for moving the head piece into a channel-like cavity by means of fluid pressure,
c) the eversion tube having, when the endoscope device is in use, an outer portion, a turning portion engaged with the head piece, and a rearwardly extending inner portion,
d) a means for exerting fluid pressure in the space between the outer portion and the inner portion of the eversion tube, which is sealed from the surroundings,
e) and a means for exerting fluid pressure in the space between the endoscope tube and the rearwardly extending inner portion of the eversion tube. Subject matter of the invention is furthermore a device for introducing an endoscope into a channel-like cavity, comprising the following features:
a) a flexible eversion tube having, when the device is in use, an outer portion, a turning portion for engagement with a head piece of the endoscope, and a rearwardly extending inner portion,
b) a means for exerting fluid pressure in the space between the outer portion and the inner portion of the eversion tube, which is sealed from the surroundings,
c) and a means for exerting fluid pressure in the space on the inside of the rearwardly extending inner portion of the eversion tube.

This device differs from the endoscope device indicated in the preceding paragraph in that it does not contain the endoscope (tube) proper, but rather is intended to be used together with the endoscope proper.

The document DE-C-28 23 025 reveals a device for transporting a coloscope into the colon, making use of a flexible eversion tube. However, in this known device the front end of the coloscope is brought in a position permitting examination of the colon only after the eversion tube has been fully extended. In contrast therewith, in the device according to the invention the cavity of interest, in particular the colon, can be inspected continuously along its length still during movement of the endoscope thereinto.

The document DE-A-24 06 823 reveals a catheter adapted to be introduced into a body cavity by means of a flexible eversion tube. It is mentioned therein that the catheter may also have a fiber glass optical system for viewing the interior. In an embodiment described therein, the catheter has a head piece engaged by a turning portion of the eversion tube. However, the eversion tube is turned up twice, so that three eversion tube portions located on top of each other are formed and no rearwardly extending inner eversion tube portion is provided. This causes excessively high frictional forces during introduction of the catheter.

None of the two known devices provides the feature that pressurized fluid is provided in the space between the endoscope tube or catheter tube and a rearwardly extending inner portion of the eversion tube.

The device according to the invention has the desired properties mentioned hereinbefore. The endoscope—apart from the initial phase in which the endoscope head is pushed through the anus—is no longer pushed or slid into the body from the outside, but moves into the body by means of propulsion of its own.

The invention is suited for all kinds of endoscopes, however, it is particularly suited for coloscopes, i.e. endoscopes for exploring the colon. The following description thus is directed to coloscopes, however, with all statements made being analogously applicable for other endoscopes as well.

Furthermore, it is pointed out that the self-propulsion according to the invention may either be incorporated in the endoscope or may be formed and sold as an additional part or supplementary part for endoscopes of a construction used so far.

According to a particularly preferred development of the invention, the self-propulsion comprises a chamber which is adapted to be acted upon by fluid pressure and preferably is of annular cross-section and which is located between an outer turned-back or everted portion of a flexible hollow member and an inner portion of the hollow member, with the chamber being sealed at its end remote from the everted end, so that fluid pressure in the chamber exerts propulsive inner pressure onto the everted end, thereby moving an increasing length of the hollow member into the intestine along with a migrating motion of the everted end. Preferably a sliding seal of the rear chamber end is provided. The hollow member preferably has only slight resilience in radial direction so that the chamber configuration in the form of an elongate annular gap shape is retained. The outer everted or turned back portion of the hollow member may or may not abut the intestinal wall.

It is possible to apply fluid pressure to the annular space between the inner portion of the hollow member and the endoscope tube during introduction. Frictional engagement with an undesirably high pressing force between the inner portion of the hollow member and the outer circumference of the endoscope tube can be avoided in this manner.

The colon consists—successively inwardly from the anus—of rectum, colon sigmoideum, colon descendens, colon transversum, and colon ascendens, with said colon sections each merging with each other with a bend of approx. 90°. The rectum can be examined comparatively easily, digitally and by rectoscopy. Examination of the rectosigmoid also can still be carried out in comparatively uncomplicated manner, since only one intestinal bend has to be passed with conventional insertion of the coloscope. Examination of the rectosigmoid in fact reveals about 60 percent of all colon tumors, however, optimum results are obtained by total coloscopy only, and the latter is made available by the device according to the invention for genuine mass application, for instance in the form of a general medical checkup starting from a specific age. Due to the self-propulsion according to the invention, the endoscope tube or guide member follows the intestinal bends much more easily than a conventional coloscope. Pushing in of the coloscope with external force application and, resulting therefrom, pressing of the endoscope tube against the intestinal wall in the region of the intestinal bends with great force do not take place, except for the easily manageable passage of the anus at the very beginning of the insertion operation. This results in quite considerable staff savings for the examinations.

Coloscopes usually have endoscope tube lengths approximately in the range from 600 to 1700 mm. It is emphasized that most embodiments of the device according to the invention are also suitable for subsequent installation or as extra equipment for the coloscopes known so far.

Figure 2:
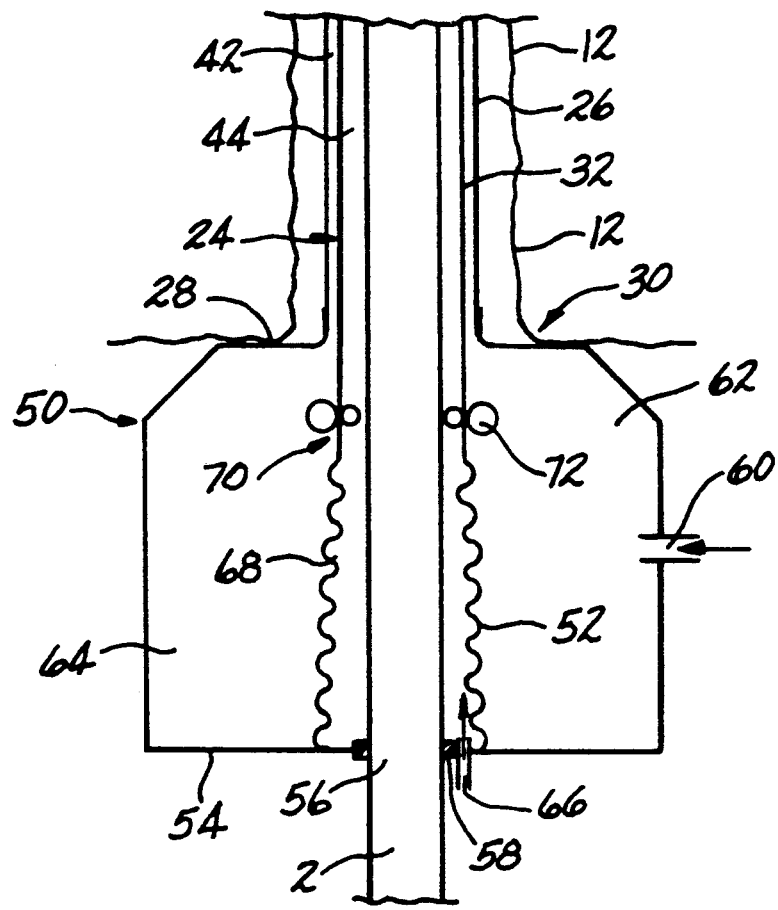

The invention and developments of the invention will be elucidated in more detail hereinafter by way of schematic embodiments shown in the drawings in which FIG. 1 shows an endoscope device in a schematic longitudinal sectional view, for illustrating the functional principle of the invention;

FIG. 2 shows the rear portion of a modified endoscope device for illustrating further details.

The main constituent part of the self-propulsion shown in FIG. 1 is a hollow member or flexible eversion tube 24, consisting for instance of rubber or a deformable plastics material. Part of the length of eversion tube 24 is turned back outwardly and constitutes an outer everted portion 26 of eversion tube 24. At its rear end, the turned back portion 26 is connected to a stiff abutment ring 28 supported on the anus 30 from the outside. The non-everted, inner portion 32 of eversion tube 24 extends outwardly from anus 30. Portions 26 and 32 merge with each other at a turning portion 34 describing a 180° bend. Within the inner portion 32, there is provided a stiff sleeve 36 extending outwardly approximately from the anus 30. The forward end of sleeve 36 is in the form of a sealing lip on the outside. Abutment ring 28, on the inner circumference thereof, also has a sealing lip. In this manner, the chamber between the outer portion 26 of the eversion tube 24 and the inner portion 32 of the eversion tube 24 (to the extent located within the colon) is sealed towards the outside.

A head piece 38 of the endoscope tube 2 is located on the turning portion 34. Head piece 38 has on its rear side a continuous, axially rearwardly directed recess or channel 40, with the eversion end 34 being seated in this recess 40.

When the chamber 42 described is subjected to fluid pressure, pressure is exerted on the turning portion 34 from the inside, which moves the head piece 38 progressively forwardly into the colon. During this inward movement, the turning portion 34, so to speak, rolls with a sliding motion in recess 40. The outer portion 26 remains stationary and becomes increasingly longer. The inner portion 32 moves into the colon approximately at twice the speed of the endoscope tube 2 and also becomes increasingly longer.

Portions 26 and 32 each run about concentrically with respect to endoscope tube 2 and extend along the colon. Portions 26 and 32 should have such stiffness in radial direction that they do not bulge excessively outwardly and inwardly, respectively, within chamber 42 under the fluid pressure. For this purpose, for instance a suitable fiber or fabric insert may be provided in the material of the eversion tube 24. It is to be understood that the abutment ring 28 is to be held against the anus 30 so that it is not pushed outwardly by the fluid pressure of chamber 42. In a modified embodiment, fluid pressure can also be applied in the elongate annular gap space 44 between the inner portion 32 of the eversion tube 24 and the outer circumference of the endoscope tube 2. This fluid pressure assists in keeping inner portion 32 spaced from endoscope tube 2, so that no substantial frictional forces are created here. This annular gap 44 is at least substantially sealed at the forward end, by the engagement between turning portion 34 and recess 40. Smaller fluid losses are not disturbing there.

Head piece 38 in particular has a camera chip (not shown) installed therein, so that the interior intestinal wall can be optically inspected during inward movement of head piece 38 and endoscope tube 2.

FIG. 2 depicts a possibility of a modified design of the rear end portion of the device.

Abutment ring 28 is secured at a front end of a pressure chamber 50. The inner portion 32 of the eversion tube 24, which extends outwardly from the anus 30, merges in pressure chamber 50 with a supply or storage portion 52 of the eversion tube 24. In this supply portion 52, the eversion tube 24 is disposed in zig-zag or corrugated manner. The rearward, in FIG. 2 lower end of the supply portion 52 is attached to the rear wall of pressure chamber 50.

The rear wall 54 of pressure chamber 50 has a central opening 56 through which the endoscope tube 2, sealed by an annular seal 58, extends rearwardly outwardly. Pressurized fluid can be supplied through an opening 60 into the portion 62 of the pressure chamber between the supply portion 52 of the eversion tube 24 and the peripheral wall 64 of the pressure chamber 50. Furthermore, pressurized fluid can be supplied through an opening 66 into the portion 68 of the pressure chamber 50 located between the endoscope tube 2 and the supply portion 52 of the eversion tube 24. Supply of the fluids takes place, for instance, by means of suitable pumps or from pressure supply containers.

It is preferred in general that a gaseous pressurized fluid is fed into the space between the outer portion 26 and the inner portion 32 of the eversion tube 24 for moving the endoscope forwardly, and that a liquid is supplied into the space 44 between the inner portion 32 of the eversion tube 24 and the endoscope tube 2 for maintaining the distance. It is best when both fluids have approximately the same pressure in said two spaces. FIG. 2 shows that the above first-mentioned space communicates with the portion 62 of the pressure chamber 50 and that the above second-mentioned space communicates with the portion 68 of the pressure chamber 50.

As an alternative, it is possible to subject the space 68 in pressure chamber 50 under pressure, not from an external pressure source through the opening 66, but—at least substantially—from the portion 62 of the pressure chamber 50 via the supply portion 52. In doing so, care must only be taken that portion 68 has such an initial volume that it balances the progressive increase in the space between the inner portion 32 of the eversion tube 24 and the endoscope tube 2 during movement of the endoscope into the intestine, by a progressive decrease of said portion 68 together with a simultaneous shift of the supply portion 52 more and more towards the center.

FIG. 2 finally shows in a schematic view a driving means for retracting the inner portion 32 of the eversion tube 24. This means 70 consists in essence of a number of roller pairs 72 mounted in annularly distributed manner in the forward portion of pressure chamber 50. A distance outside from anus 30, the inner portion 32 of eversion tube 24 is passed through the ring of roller pairs 72 before merging with the supply portion 52. At least some of the rollers of the roller pairs 72 are adapted to be driven by miniaturized electric motors, not shown. Upon driving rotation of these roller pairs 72 in the proper direction of rotation, the inner portion 32 of the eversion tube 24 is pulled outwardly from the intestine. At the same time, a pulling force is expediently exerted on the endsocope tube 2, so that the head piece 38 substantially remains in contact with the turning portion 34 of the eversion tube 24. The pressure in the fluid space between the outer portion 26 and the inner portion 32 of the eversion tube 24 can be reduced simultaneously. During such controlled retraction of the endoscope, the intestinal wall can be inspected once more.

The turning portion 34 of the eversion tube 24 need not necessarily be engaged with a rear recess 40 of the head piece 38. It is also possible to provide engagement with a continuous recess extending along the outer circumference of the head piece 38. In this case, an outer ring must be provided holding the turning portion 34 in the outer circumferential recess against displacement in the longitudinal direction of the endoscope tube 2. This ring may comprise a number of annularly arranged balls or rollers. With this embodiment, the endoscope tube 2 is retracted together with the retraction of the inner portion 32 of the eversion tube 24.

In the drawings reference numeral 14 designates the colon and reference numeral 12 the intestinal or colon wall.

In accordance with an alternative configuration possibility the supply portion 52 of the eversion tube 24, inclusive of the part of the endoscope tube 2 located therein, is deposited in the pressure chamber 50 in the form of bends or S-shaped loops of relatively large radius of curvature. The supply portion 52 then need not be corrugated in itself.

It is pointed out that the driving means may also be realized with an endoscope device including no fluid pressure exertion in the space on the inside of the rearwardly extending, inner portion of the eversion tube.

We claim:
1. An endoscope device comprising:
   a) an endoscope tube having a head piece;
   b) a flexible eversion tube for moving the head piece into a channel-like cavity by means of fluid pressure;
   c) the eversion tube having, when the endoscope device is in use, an outer portion, a turning portion engaged with the head piece, and an inner portion extending away from said head piece;
   d) means for exerting a first fluid pressure in a space between the outer portion and the inner portion of the eversion tube, which space is sealed from ambient surroundings; and
   e) means for exerting a second fluid pressure in a space between the endoscope tube and the inner portion of the eversion tube.

2. The endoscope device of claim 1 wherein said turning portion engages a continuous recess in said head piece.

3. The endoscope device of claim 1 further including a driving means for retracting said inner portion of said eversion tube.

4. The endoscope device of claim 1 further including a fluid pressure supply portion for said eversion tube which supply portion is disposed in a pressure chamber whose pressure acts between the outer portion and the inner portion of the eversion tube.

5. The endoscope device of claim 1 wherein the first fluid pressure in the space between the outer portion and the inner portion of the eversion tube is created by a gas, and the second fluid pressure in the space between the endoscope tube and the inner portion of the eversion tube is created by a liquid.

6. A device for introducing an endoscope into a channel-like cavity, said device comprising:
   a) a flexible eversion tube having, when in use, an outer portion, a turning portion adapted for engagement with a head piece of the endoscope, and a rearwardly extending inner portion;

b) first means for exerting fluid pressure in a space between the outer portion and the inner portion of said eversion tube, which space is sealed from ambient surroundings; and c) second means for exerting fluid pressure in a space on the inside of the rearwardly extending inner portion of the eversion tube to prevent any part of said inner portion disposed rearwardly of said turning portion from contacting the endoscope so as to minimize generation of frictional forces between said inner portion and the endoscope.

7. The device of claim 6 further including a driving means for retracting said inner portion of said eversion tube.

8. The device of claim 6 further including a fluid pressure supply portion for said eversion tube which supply portion is disposed in a pressure chamber whose pressure acts between the outer portion and the inner portion of the eversion tube.

9. The device of claim 6 wherein said first exerts a gas fluid pressure in the space between the outer portion and the inner portion of the eversion tube said second means exerts a liquid and fluid pressure in the space on the inside of the inner portion of the eversion tube.

* * * * *